United States Patent [19]

Quint

[11] Patent Number: 5,084,044

[45] Date of Patent: Jan. 28, 1992

[54] APPARATUS FOR ENDOMETRIAL ABLATION AND METHOD OF USING SAME

[75] Inventor: Robert H. Quint, Jamaica, N.Y.

[73] Assignee: Ciron Corporation, Santa Barbara, Calif.

[21] Appl. No.: 380,200

[22] Filed: Jul. 14, 1989

[51] Int. Cl.⁵ .............................................. A61B 17/36
[52] U.S. Cl. ................................... 606/27; 606/191; 606/192; 604/96; 128/401
[58] Field of Search .................................. 606/27–31, 606/7, 191–194, 196–198; 604/95, 96; 128/303.1, 395–403

[56] References Cited

U.S. PATENT DOCUMENTS 3,924,628 12/1975 Droegemuller et al.
4,949,718 9/1990 Neuwirth.

Primary Examiner—Robert A. Hafer
Assistant Examiner—Kerry Owens

[57] ABSTRACT

Apparatus for performing thermal ablation of the endometrium of a uterus is shown. The apparatus includes a catheter having at least one lumen. An insulating material is positioned around a selected portion of the exterior of the catheter to insulate the same from the walls of the vagina. A thermally conductive inflatable member is operatively coupled to the distal end of the catheter. The inflatable member is capable of expanding from a collapsed position, when filled with a fluid, into an expanded position which approximates the shape and volume of a uterus. The inflatable member is adapted to be placed into the uterus in the collapsed position and is filled through the catheter with a heated fluid to expand the inflatable member into its expanded position and into intimate contact with the endometrium. The heated fluid has a selected temperature and the inflatable member is capable of thermally conducting heat from the fluid to the endometrium for a period of time to thermally ablate selected tissue or ablate tissue to a selected depth. The thermal ablation apparatus may also be used to perform ablation of any mucosa layer in an organ of a body such as the gall bladder or large intestine.

A method for using the thermal ablation apparatus in a surgical procedure is also shown.

27 Claims, 2 Drawing Sheets

FIG. 1
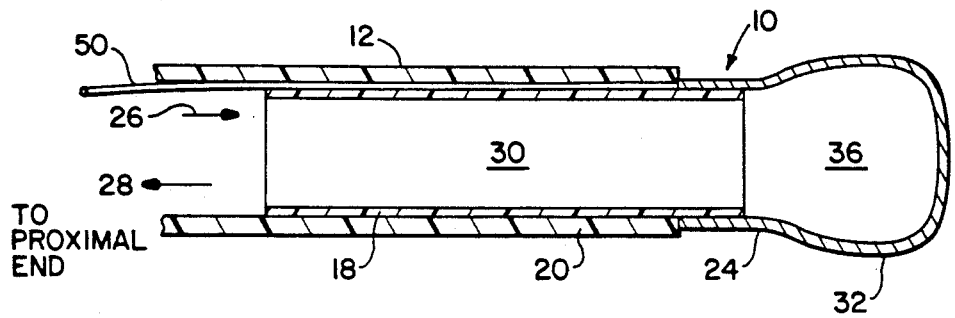
FIG. 2
FIG. 3
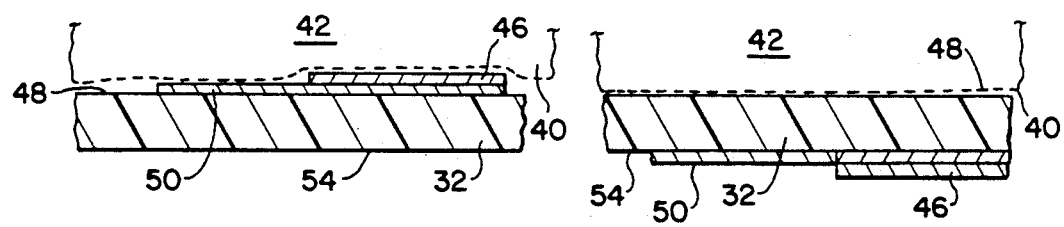
FIG. 4
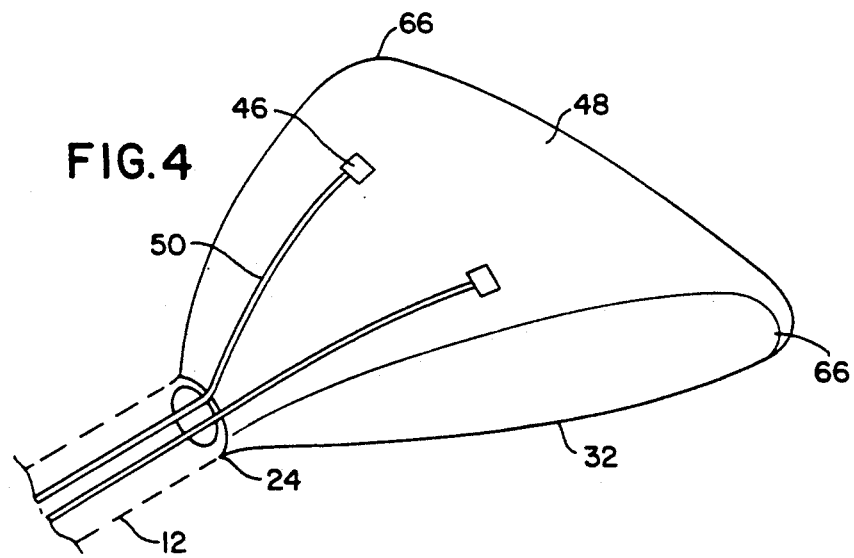

APPARATUS FOR ENDOMETRIAL ABLATION AND METHOD OF USING SAME

BACKGROUND OF THE INVENTION

1. Field of the Invention

This invention relates to an apparatus which utilizes heated fluid for controllably thermally ablating tissue in a body cavity and more particularly relates to an apparatus for performing thermal ablation of the endometrium of a uterus by use of an insulated catheter having a thermally conductive inflatable means.

2. Description of the Prior Art

It is well known in the art to use heated fluid for treatment of the human body. One such known device is a hot water bottle which is used to apply heat locally to a selected portion of the body. The temperature of the heated fluid is typically maintained at a level that does not burn the body or thermally damage the tissue.

It is also know in the art to utilize what is referred to as the "Elliot Treatment" machine or the "Elliot treatment regulator" to thermally treat selected regions of the body. The "Elliot treatment regulator" has thin rubber applicators which are adapted to have heated water circulated therethrough under pressure. In use, the thin rubber applicators are placed into contact with selected regions of the body. The temperature and pressure of the water passed through the thin rubber applicators can be controlled accurately. Rubber applicators having various sizes and shapes have been fabricated for numerous applications. Specifically, rubber applicators have been fabricated for vaginal and rectal applications, e.g. for direct application of heat to the large intestine.

In the known vaginal application using the above described device, a vaginal applicator was fabricated to fit into the fornices of the vagina. When the vagina applicator was distended by pressure, the applicator functioned to apply heat directly to and "iron out" the vaginal rugae and came in contact with a layer portion of the mucosa. The above application used conductive heat because it was the most superficial and because there was less penetration.

An excellent summary of known prior art devices for heat treatment, including those briefly described above, and a description of the other related effects thereof such as: (1) physiologic effects of local heating; (2) technic of local application of heat; (3) indications for the employment of local heating; (4) contraindications to and dangers and limitations of local application of heat; and (5) conclusions with regard to local applications of conductive heat are set forth in a Reference Book entitled *PHYSICAL MEDICINE* published by W. B. Saunders, 1941, written by F. Krusem, M.D., at pages 156 through 165 (the "Physical Medicine Reference") The Physical Medicine Reference at pages 158, 159 sets forth the following summary concerning temperatures relating to use of heat for treatment of the human body:

"The physiologic basis for the employment of heat has been well reviewed by Bazett. In spite of the fact that it is generally considered that a temperature of 98.6° F. (37° C.) exists throughout the normal human body, actually the temperature of the blood in peripheral regions is fare below the central temperature. Temperatures of skin, fat and muscle in peripheral regions are variable and considerably lower than the rectal temperature. Local applications of heat will tend to bring the temperature in peripheral regions to higher levels. Bazett calculated the temperature limit beyond which tissues are damaged, at least by loca hot baths, at approximately 113° F. (45° C.). If baths of this temperature are employed for an hour or more, edema may be noted which will last for twelve to twenty-four hours. Most observers believe that dry hot air temperatures of much higher degrees can be tolerated, however, The vaginal mucosa will tolerate considerably higher temperatures of conductive heat than will the skin; the former apparently is able to withstand temperatures of 116° F. (46.6° C.) for many hours and temperatures of 125° F. (51.7° C.) for short periods of time up to one hour. Variations in the temperature of the skin, subcutaneous tissues and superficial muscle fibers may exceed 36° F. (20° C.) for short periods of time without such changes being necessarily injurious.

When heat is applied locally, blood vessels become dilated and the rate of the flow of blood is increased. The increase in the rapidity of circulation intensifies the thermal conductivity of the tissues and tends to distribute the heat throughout the body, thus hindering the rise in local temperature. Local applications of heat, therefore, always tend to produce a generalized increase of temperature. On exposure to heat, transference of fluid from the blood to the tissues will be increased. When the blood is warmed, the acidity and the carbon dioxide tension are increased. It has been suggested that the changes in tension of cabon dioxide, and possibly also those in acidity, may be of some value in modifying the reactions of tissues to infections. There is evidence that local applications of heat increase phagocytic and local metabolic activity."

It is know in the art to use other techniques and/or apparatus for endometrical ablation of the uterus. One known method utilizes a YAG Laser through an endoscope to destroy tissue of the endometrium to coagulate blood stopping bleeding, to resect fibroids and the like. Also, it is known in the art to use electrosurgical techniques to obtain substantially equivalent results as that of the YAG Laser wherein a radio frequency electrosurgical current is applied through a roller ball electrode of a resectoscope to the endometerium performing endometrial ablation.

SUMMARY OF THE PRESENT INVENTION

This invention relates to a new, novel and unique apparatus for performing controlled thermal ablation of tissue within a cavity. In the preferred embodiment, the apparatus is used for performing thermal ablation of the endometrium of a uterus. The apparatus comprises means defining a catheter having an exterior surface, at least one lumen, a distal end and a proximal end. An insulating means is positioned around the exterior surface of the catheter and extend over a selected portion thereof intermediate the distal end and the proximal end. A thermally conductive inflatable means is operatively coupled to the distal end of the catheter. The inflatable means is capable of being expanded when filled with a fluid from a collapsed position into an expanded position which approximates the shape and volume of a uterus. The inflatable means in the collapsed position when placed into the uterus and when filled through the catheter with a heated fluid having a selected temperature is capable of being urged into the expanded position and into intimate contact with the endometrium and thermally conducting heat from the fluid to the endometrium for a predetermined period of time to thermally ablate selected tissue from the endometrium.

Also, disclosed is a surgical procedure and method for using the thermal ablation apparatus. The method for performing thermal ablation of the endometrium of a uterus comprises the steps of inserting into the cervical canal a thermal ablation apparatus comprising a catheter having a distal end and a proximal end with an insulating means located around the catheter and a thermally conductive inflatable means operatively coupled to the distal end of the catheter wherein the inflatable means is capable of expanding when filled with a fluid from a collapsed position into an expanded position which approximates the shape and volume of a uterus. The catheter is transported with the distal end thereof into and through the vagina, through the cervix into the uterus into the insulating means located around the catheter in contact with and insulating the wall of the cervical canal and being inserted a sufficient distance to place the distal end and such inflatable means in the collapsed position into the uterus. Thereafter, the method includes the steps of passing a predetermined volume of heated fluid at a selected temperature from the proximal end of and through the catheter into the inflatable means to expand the same into its expanded position urging the surface of the inflatable means into intimate contact with the endometrium of the uterus; controlling the period of time that the heated fluid is in intimate contact with the endometrium while enabling the inflatable means to thermally conduct heat from the heated fluid to the endometrium to ablate a predetermined thickness of tissue therefrom; and removing the heated fluid from the inflatable means after the period of time.

In addition, the above method may further comprise the step of thermally sensing the temperature of the endometrium during the period of time that the thermally conductive inflatable means is thermally conducting heat from the heated fluid to the endometrium.

In the known prior art devices, such as the "Elliott treatment regulator" applicators are used to apply heat to selected areas of the body to cause some physical changes, e.g. increased blood flow, without causing damage to the tissue. The use of thin rubber applicators in a vaginal application applies heat to the walls of the vagina. If the temperature of the heated fluid is elevated to a high temperature in excess of about 122° F. (50° C.), damage could occur to the tissue of the vaginal walls.

Further, the use of the YAG Laser and use of a roller ball electrode through a resectoscope requires the user to have special skills and good techniques to avoid undesirable tissue damage or to avoid too great of depth of penetration into or destruction of the endometrium.

The present invention overcomes the disadvantages of the prior art apparatus and surgical techniques.

Specifically, one advantage of the present invention is in that the thermal ablation apparatus provides the user with an instrument that is capable of fairly precisely controlling depth of tissue destruction within a cavity of the body by controlling the temperature of a heated fluid and the period of time that the heated fluid is brought into intimate contact, through a thermally conductive member, with the tissue to be ablated.

Another advantage of the present invention is that the thermal ablation apparatus includes an insulated catheter which, when inserted into the cervical canal of a female, protects the side walls of the cervical canal and cervix from being ablated.

Another advantage of the present invention is that the thermal ablation apparatus can be used in a system which includes temperature sensing means, heated fluid flow channels including pump, heater and the like, to precisely control the temperature of the heated fluid and flow rates of the heated fluid within the thermal ablation apparatus.

Another advantage of the present invention is that the thermal ablation apparatus can be used in a surgical procedure for controllably ablating the endometrium of a uterus to a selected depth of penetration.

Another advantage of the present invention is that the heated fluid can be selected to be a fluid which is safe from chemical interaction with the patient. In the preferred embodiment, the preferred fluid is a saline solution. The temperature range of the heated fluid is from about 122° F. (50° C.) to about 214° F. (99° C.), and the ablation times, e.g. period the heated fluid is in intimate contact with the endometrium of the uterus, is in the order of about 30 seconds to about 10 minutes, the shorter time being associated with higher temperature.

BRIEF DESCRIPTION OF THE DRAWING

These and other advantages of the invention will be readily apparent when considered in light of the detailed description hereinafter of the preferred embodiment and when considered in light of the drawing set forth herein which includes the following Figures:

FIG. 1 is a partial cross-section pictorial presentation of a thermal ablation apparatus using the teachings of the present invention;

FIG. 2 is a diagrammatic representation of a thermally conductive inflatable means having a temperature sensing means on the surface thereof which is in intimate contact with the endometrium;

FIG. 3 is a diagrammatic representation of a thermally conductive inflatable means having a temperature sensing means on the surface opposite the surface thereof which is in intimate contact with the endometrium;

FIG. 4 is a partial perspective view of the thermally conductive inflatable means in the expanded position;

DESCRIPTION OF THE PREFERRED EMBODIMENT

Figure 5:
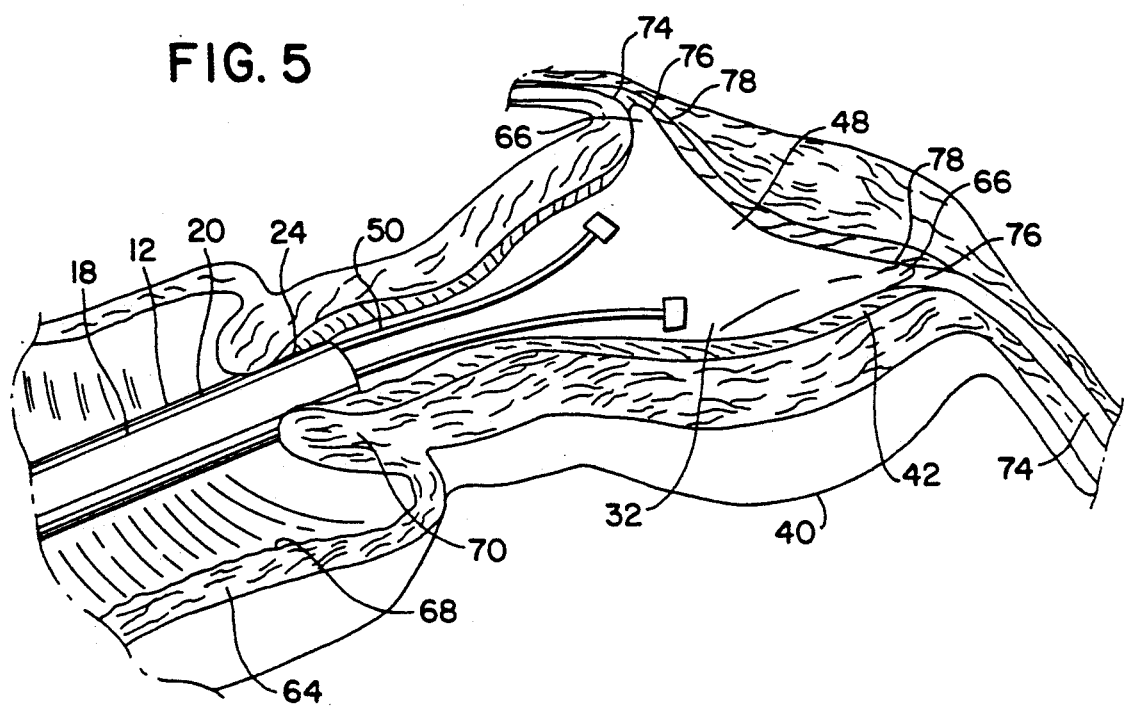
FIG. 5 is a partial perspective view of a uterus having the thermal ablation apparatus inserted therein to perform the method of thermal ablation of the endometrium.

FIG. 1 depicts pictorially apparatus for performing controlled thermal ablation of tissue within a cavity of the body. The apparatus, shown generally as 10, includes means defining a catheter 12. The means defining the catheter 12 may be formed by a thin walled, elongated cylindrical shaped member 18 which has an insulating means 20 positioned therearound intermediate the distal end 24 and the proximal end 28. Catheter 12 is shown pictorially as having one lumen 30. The catheter 12 may be formed from an insulating material which defines at least one lumen in the catheter.

A thermally conductive inflatable means 32 is operatively coupled to the distal end 24 of the catheter 12. The inflatable means 32 is capable of being expanded, when filled with a fluid, from a collapsed position, illustrated to have an interior size 36 in FIG. 1, into an expanded position having a preselected shape and volume, as illustrated in FIG. 4.

The inflatable means 32, in a collapsed position, is placed into the body cavity, e.g. uterus, colon, gallbladder or the like, and is then filled through the catheter with fluid which can be heated to a selected temperature. The fluid may be heated prior to or during the passing of the same into the inflatable means 32 or heated within the inflatable means 32. The heated fluid is capable of urging the inflatable means 32 into the expanded position and into intimate contact with the tissue within the cavity. The inflatable means 32 is selected to be formed of a resilient, thermally conductive material which is biocompatible with the body. If desired, the external surface of the inflatable means can be coated with or formed to be a release material to prevent sticking to the cavity, e.g. the uterus. The inflatable means 32 thermally conducts heat from the heated fluid to the tissue for a predetermined period of time to thermally ablate to a predetermined depth selected tissue from the cavity.

In the preferred embodiment, the body cavity is the uterus. However, the thermal ablation apparatus could be used to perform ablation of any mucosa tissue in an internal organ of the body, such as the gallbladder or large intestine. The thermal ablation apparatus 10 would preferrably be used to perform an endometrial ablation procedure in the uterus to obtain results which are surgically functionally equivalent to those obtained with a YAG Laser and roller ball devices.

FIGS. 2 and 3 illustrate the apparatus for performing thermal ablation of the endometrium 40 of the uterus shown generally as 42. In FIGS. 2 and 3, the thermally conductive inflatable means 32 includes temperature sensing means 46 located on a selected surface. As shown in FIG. 2, the selected surface is surface 48. Surface 48 is adapted to be placed into intimate contact with the endometrium 40 of the uterus 42. The temperature sensing means 46 is operatively connected to a flexible conducting means 50 (also shown in FIG. 1) which is used to conduct electrical signals between the temperature sensing means 42 and a control circuit 92 shown in FIG. 6.

FIG. 3 shows an alternative embodiment to FIG. 2 wherein the selected surface having the temperature sensing means 46 affixed thereto is an inner surface 54 of the inflatable means 32. Surface 54 is opposite to the surface 48 that is adapted to be placed into intimate contact with the endometrium 40 of the uterus 42. The heat transfer characteristics of the material used to fabricate the inflatable means 32, will result in a thermal drop thereacross. In calculating heat transfer rates, efficiency, time of heat transfer and the like to determine depth of penetration, it is possible to compensate for the thermal losses of this inflatable material thereby achieving the same desired results as with either embodiment.

FIG. 4 illustrates the shape and configuration of the inflatable means 32 when expanded outside of a cavity. Generally, the inflatable means has a pair of opposed, spaced extended arms 66 that have a shape and dimension that enables the extended arm 66 to seal the orifices to the fallopian tubes as described in greater details in connection with the description of FIG. 5. The inflatable member 32 is selected to be formed of an elastomeric material and conform to the shape of the organ under pressure derived from the fluid passed into the inflatable means. The extended arms 66 may become long and thin as shown in FIG. 5 in order to conform to the shape of the uterus.

The temperature sensing means 46 are shown being affixed to the exterior surface 48 of the inflatable means 32. Conductive means 50 extend from the temperature sensing means to the catheter 12. As shown in FIG. 1, the conductive means 50 are preferably located between the thin walled, elongated cylindrical shaped member 18 and the insulating means 20 or internal to the catheter 12.

FIG. 5 illustrates the thermal ablation apparatus 10 inserted through the vagina 64, having walls 68 with the distal end 24 of the cather 12 extending through the cervix 70 and into the uterus 40. As shown in FIG. 5, the uterus communicates with a pair of fallopian tubes, shown generally as 74, which have an orifice shown generally as 76. The area of the uterus narrows as it approaches the orifice of the fallopian tubes is known as the cornua, and this is shown as element 78. The extended arms 66 extend into the orifices 76 to insure that heat transfer will not occur into the fallopian tubes 74 to prevent thermal ablation thereof.

In the preferred embodiment, the method for thermal ablation of the endometrium 42 of the uterus 40 comprising the following steps:
  inserting a thermal ablation apparatus 10 comprising a catheter 12 having a distal end 24 and a proximal end 28 with an insulating means 20 located around the catheter 12 and a thermally conductive inflatable means 32 operatively coupled to the distal end 24 of the catheter 12 wherein the inflatable means 32 is capable of expanding when filled with a fluid 26 from a collapsed position into an expanded position which approximates the shape and volume of a uterus 40, into and through the vagina 64 with the distal end 24 directed towards the uterus, through the cervix 70 and into the uterus 40 positioning the insulating means 32 located around the catheter 12 adjacent the walls of the vagina and being inserted into the uterus 40 a sufficient distance to place the distal end 24 and inflatable means 32, in the collapsed position, into the uterus 40;
  passing a predetermined volume of heated fluid 26 at a selected temperature from the proximal end 28 of and through said catheter 12 into the inflatable means 32 to expand the same into its expanded position urging the surface 48 of the inflatable means 32 into intimate contact with the endometrium 42 of the uterus 40;
  controlling the period of time that the heated fluid 12 is in intimate contact with the endometrium 42 while enabling the inflatable means 32 to thermally conduct heat from the heated fluid to the endometrium 42 to ablate a predetermined thickness of tissue therefrom; and
  removing the heated fluid 12 from the inflatable means 32 after the selected period of time.

In addition, the method could further comprise the step of thermally sensing the temperature of the endometrium 42 during the period of time that the thermally conductive inflatable means 32 is thermally conducting heat from the heated fluid 12 to the endometrium.

After the procedure is completed, the method would further comprise the step of deflating the inflatable means 32 into its collapsed position by removing fluid 12 therefrom; and withdrawing the catheter 12 having the inflatable member 32 in a colapsed position from uterus 40, through the cervix 70 and out of the vagina 64.

Figure 6:
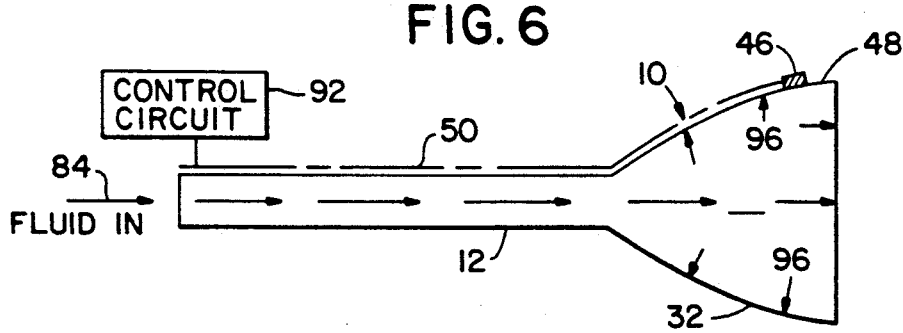
FIG. 6 is a pictorial representation of a system in which heated fluid is passed through the insulated catheter into the thermally conductive inflatable means.
Figure 7:
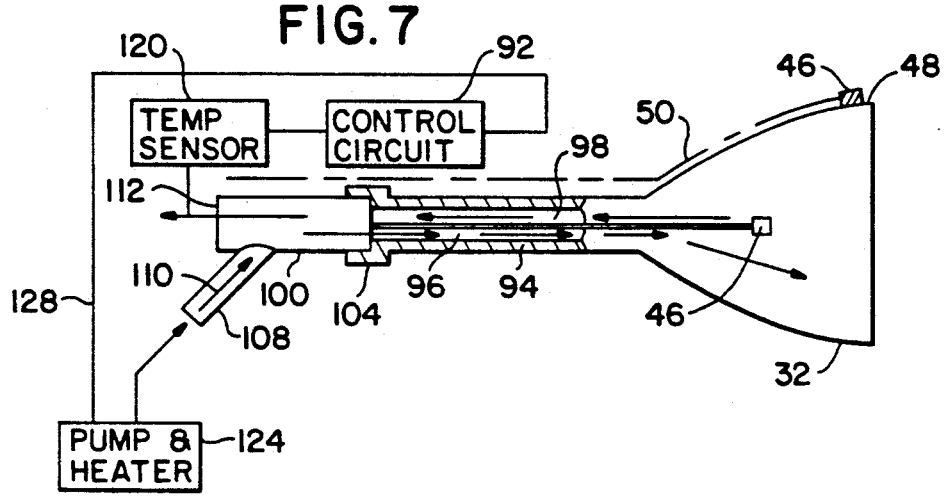
FIG. 7 is a pictorial representation of a thermal ablation system using a double lumen catheter for practicing the teachings of the present invention.

FIG. 6 shows one embodiment of a system comprising the thermal ablation apparatus 10 having the temperature sensing means 46 affixed to the exterior surface 48. Conductive means 50 operatively extend from the temperature sensing means 46 to a control circuit 92 located exterior to the apparatus 10. Heated fluid, depicted by arrow 84, is passed through the catheter 12 into the inflatable means 32 expanding the same by the pressure of the heated fluid depicted by arrow 96. The inflatable means 32, when expanded, has an interior cavity 80 having a volume substantially equal to that of the uterus as described in connection with FIG. 5.

The temperature sensing means 46 and the control circuit 92 provide the user to monitor the temperature of the heated fluid in the inflatable means 32. If a malfunction occurred, if e.g. the heated fluid exceeds a safe maximum temperature, the user can immediately withdraw the heated fluid from the inflatable means 32 or add or exchange fluid to reduce the temperature thereof or take other appropriate remedial action.

FIG. 6 describes an alternative embodiment of a system for practicing this invention using a double lumen catheter 94 having lumens 96 and 98. The catheter 94 may be fabricated from an insulating material, or may be fabricated from two separate materials in the manner as that of catheter 12 described in connection with FIG. 1.

A "Y" shaped connector 100 is operatively attached to the distal end 104. The connector 100 includes means for directing fluid flow in a first direction, such as for example an inlet 108 for lumen 96 to pass a fluid shown by arrow 110 through lumen 96 into the interior cavity 80 of the inflatable means 32. Also, connector 100 include means for directing fluid flow in a second direction opposite to the first direction, such as, for example, an outlet 112 for lumen 98 to withdraw fluid through lumen 98 from the interior cavity 80 of the inflatable means 32.

By using the above described double lumen catheter 94 and connector 100, a bi-direction or continuous flow catheter can be provided to maintain fluid flow and pressure to the inflatable means 32. In this manner, the temperature and pressure of the heated fluid flow can be precisely controller.

The system control means depicted in FIG. 6 would include the temperature sensing means 46, the conductive means 50 which is operatively connected to the control circuit 92 and temperature sensor and control 120 pump and heater 124. The control circuit 92 is operatively connected via a lead 128 to the pump and heater control 124.

The systems shown in FIGS. 5 and 6 are two embodiments for using either a single lumen catheter or double lumen catheter as a thermal ablating device. It is envisioned that the control circuit could be a computer having appropriate programs and memory means. Also, the thermal ablation apparatus could be a sub-assembly of an instrument which includes a telescope or fiberoptic bundle to produce an optical image of the cavity. A video imaging means, such as a beamsplitter video camera could be used with the telescope and/or fiberoptic bundle to produce a video image of the procedure.

Further, the thermal ablation apparatus may be fabricated to be rigid or flexible instrument, depending on the application.

In certain other applications, the thermal ablation device could be used in a cavity other than a human body, such as for industrial application to thermally remove material layers from an internal surface of a remote cavity.

In certain application, and depending on the restriction as to the diameter of the apparatus, an evacuation channel may be provided or, in the case of the double lumen catheter, the one of the two lumens could be used as an evacuation channel and have a negative pressure or vacuum applied thereto. The negative pressure or vacuum, e.g. reverse operation of the pump 124, could also be used as a rapid withdrawel means to withdraw heated fluid from the inflatable means 32 in the event that an undesired condition is encountered or in an emergency situation.

The depth of penetration of heat into the tissue of an organ of the body, such as for example the endometrium of the uterus, resulting in ablation of selected tissue can be calculated using the following formula:

$$T - Ts = -(Ts - 37)\, erf(x/2 \sqrt{Kt}) \quad \text{Equation No: 1}$$

wherein
T = Temperature in depth (x), function of t;
Ts = Surface temperature due to fluid;
erf = error function;
x = Distance into tissue from surface;
K = Diffusion coefficient of tissue; and
t = Time The minimum amount of time necessary for tissue ablation to a depth "X", can be approximated by the following formula:

$$1 = 10^{98} \int_{o}^{t} exp[-(75{,}000)/T + 273]dt \quad \text{Equation No: 2}$$

which is a thermal damage integral equation.

By using the above equation No. 2 and using equation No. 1 as the definition of variable T (temperature) in the equation No. 2 and performing numerical integration, the depth "x" can be approximated;

For example, where $x = 1$ millimeter, $K = 10^{-3}$ and $Ts = 90°$ C., it will take about 10 seconds for ablation to occur.

What is claimed is:

1. Apparatus for performing controlled thermal ablation of tissue within a cavity of the body comprising
    means defining a catheter having a distal end and insulating means positioned around said catheter; and
    thermally conductive inflatable means operatively coupled to the distal end of said catheter, said inflatable means being capable of being expanded when filled with a fluid from collapsed position into an expanded position having a preselected shape and volume, said inflatable means being in a collapsed position when placed into the body cavity and when filled through said catheter with a fluid capable of being urged into the expanded position and into intimate contact with tissue within a cavity and when the fluid is heated to a selected temperature to thermally conduct heat from the heated fluid to tissue for a predetermined period of time to thermally ablate to a predetermined depth of selected tissue from a cavity; and means located external to and operatively coupled to the catheter means for heating a fluid to said selected temperature to cause thermal ablation of tissue and for transporting said heated fluid through the catheter means and into the thermally conductive inflatable means to thermally ablate tissue within a cavity, said fluid heating and transporting means including means for maintaining said heated fluid at said selected temperature for the predetermined period of time to thermally ablate to a predetermined depth selected tissue from a cavity.

2. Apparatus for performing thermal ablation of the endometrium of a uterus comprising means defining a catheter having an exterior surface, at least one lumen, a distal end and a proximal end;

insulating means positioned around the exterior surface of said catheter and extending over a selected portion thereof intermediate the distal end and the proximal end; and thermally conductive inflatable means operatively coupled to the distal end of said catheter, said inflatable means being capable of being expanded when filled with a fluid form a collapsed position into an expanded position which approximates the shape and volume of a uterus, said inflatable means being in a collapsed position when placed into a uterus and when filled through such catheter with a heated fluid having a selected temperature being capable of being urged onto the expanded position and into immediate contact with the endometrium and thermally conducting heat from the fluid to the endometrium for a predetermined period of time to thermally ablate selected tissue from the endometrium; and means located external to and operatively coupled to the catheter means for heating a fluid to said selected temperature to cause thermal ablation of tissue and for transporting said heated fluid through the catheter means and into the thermally conductive inflatable means to thermally ablate the endometrium of a uterus, said fluid heating and transporting means including means for maintaining said heated fluid at said selected temperature for the predetermined period of time to thermally ablate to a predetermined depth selected endometrium from a uterus.

3. The apparatus of claim 2 wherein said thermally conductive inflatable means includes temperature sensing means located on a selected surface of said inflatable means.

4. The apparatus of claim 3 wherein said temperature sensing means is located on a surface of the inflatable means that is adopted to be placed into immediate contact of the inflatable means that is adapted to be placed into intimate contact with the endometrium of a uterus.

5. The apparatus of claim 3 wherein said temperature sensing means are located on an interior surface of the inflatable means which is opposite the surface of the inflatable means that is adapted to be placed into intimate contact with the endometrium of a uterus.

6. The apparatus of claim 2 wherein a uterus to be subject to the thermal ablation of the endometrium includes two fallopian tubes each of which communicate with the uterus through an orifice and wherein said apparatus further includes thermally conductive inflatable means having a pair of opposed, spaced extended arms having a shape and dimension that enables the extended arm to make sealing engagement with each orifice of each of said fallopian tubes to prevent heated fluid from thermally ablating the walls of the fallopian tubes.

7. The apparatus of claim 2 wherein said catheter has at least one lumen.

8. The apparatus of claim 2 wherein said catheter has at least two lumens.

9. A system for performing thermal ablation of the endometrium of a uterus comprising means for heating a fluid to a temperature in the temperature range of about 122° F. (56° C.) to about 211° F. (99° C.);

means operatively connected to said fluid heating means for transporting said heated fluid;

temperature indicating means for producing a signal representing the temperature of the heated fluid;

thermal ablating apparatus comprising means defining a catheter having a distal end and a proximal end;

insulating means positioned around said catheter;

thermally conductive inflatable means operatively coupled to the distal end of said catheter, said inflatable means being capable of being expanded when filled with a fluid from a collapsed position into an expanded position which approximates the shape and volume of a uterus, said inflatable means being in a collapsed position when placed into a uterus and when filled through said catheter with a heated fluid having a selected temperature within the temperature range being capable of being urged into the expanded position and into intimate contact with the endometrium of a uterus and thermally conducting heat from the fluid to the endometrium for a predetermined period of time to thermally ablate selected tissue from the endometrium of a uterus; and temperature sensing means located on a selected surface of said inflatable means.

10. The apparatus of claim 9 wherein said thermally conductive inflatable means include temperature sensing means located on a selected surface of the inflatable means.

11. The apparatus of claim 9 wherein said temperature sensing means is located on a surface of the inflatable means that is adapted to be placed into intimate contact with the endometrium of a uterus.

12. The apparatus of claim 9 wherein said temperature sensing means is located in an interior surface of the inflatable means which is opposite the surface of the inflatable means that is adapted to be placed into intimate contact with the endometrium of a uterus.

13. The apparatus of claim 9 wherein uterus to be subject to the thermal ablation of the endometrium includes two fallopian tubes each of which communicates with the uterus through an orifice and wherein said apparatus further includes thermally conductive inflatable means having a pair of opposed, spaced extended arms having a shape and dimension that enables the extended arms to make sealing engagement with the orifice of each of said fallopian tubes to prevent heated fluid from thermally ablating the walls of the fallopian tubes.

14. The apparatus of claim 9 wherein said catheter has at least one lumen.

15. The apparatus of claim 9 wherein said catheter has at least two lumens.

16. A method for performing thermal ablation of the endometrium of a uterus comprising the steps of inserting a thermal ablation apparatus, comprising a catheter having a distal end and a proximal end with an insulating means located around the catheter and a thermally conductive inflatable means operatively coupled to the distal end of the catheter wherein the inflatable means is capable of expanding when filled with a fluid from a collapsed position into an expanded position which approximates the shape and volume of a uterus into and through the vagina with the distal end thereof being positioned toward the uterus, through the cervix and into the uterus positioning the insulating means located around the catheter adjacent the walls of the vagina and with the catheter being inserted into the uterus a sufficient distance to place said distal end and inflatable means in the collapsed position in the uterus;

passing a predetermined volume of heated fluid which is at a temperature which is in a temperature range of about 122° F. (56° C.) to about 211° F. (99° C.) from the proximal end of and through said catheter into the inflatable means to expand the same into its expanded position urging the surface of the inflatable means into intimate contact with the endometrium of a uterus;

controlling the period of time that the heated fluid is in intimate contact with the endometrium while enabling the inflatable means to thermally conduct heat from the heated fluid to the endometrium to ablate a predetermined thickness of tissue therefrom; and removing the heated fluid from the inflatable means after said period of time.

17. The method of claim 16 further comprising the step of thermally sensing the temperature of the endometrium of a uterus during the period of time that the thermally conductive inflatable means is thermally conducting heat from the heated fluid to the endometrium.

18. The method of claim 17 further comprising the step of deflating the inflatable means into its collapsed position by removing fluid therefrom; and withdrawing the catheter having the inflatable member in a collapsed position from a uterus, through the cervix and out of the vagina.

19. The method of claim 18 further comprising the step of controllably heating the heated fluid for maintaining the same at a temperature within the temperature range.

20. The method of claim 18 wherein said catheter has at least two lumens and further comprising the steps of passing a heated fluid into the inflatable means through one of the said lumens; and removing fluid from the inflatable means through the other of the said lumens.

21. The method of claim 16 further comprising the step of controlling the depth of tissue ablation as a function of the diffusion coefficient of tissue, the temperature of the heated fluid and the time the heated fluid is held by the inflatable means in intimate contact with the endometrium of a uterus.

22. The method of claim 21 wherein the step of controlling the time of and depth of ablation of tissue os determined in accordance with the following formulas:

$$T - T_s = -(T_s - 37) \, \text{erf} \, (x/2\sqrt{Kt}) \qquad \text{Equation No. 1}$$

wherein $T$ = Temperature in depth (x), function of t;
$T_s$ = Surface temperature due to fluid
erf = error function
$x$ = Distance into tissue from surface;
$K$ = Diffusion coefficient of tissue; and
$t$ = Time; and $$1 = 10^{98} \int_o^t \exp[-(75,000)/T + 273] dt. \qquad \text{Equation No. 2}$$

23. The method of claim 21 wherein the heated fluid is a saline solution and wherein the temperature of the fluid is selected to be a temperature in the range of about 122° F. (56° C.) to about 211° F. (99° C.) and the predetermined period of time is selected to be in the range of about 30 seconds to about 10 minutes.

24. A method for performing thermal ablation of a mucosa tissue of an organ of a body comprising the steps of inserting a thermal ablation apparatus comprising a catheter having a distal end and a proximal end with an insulating means located around the catheter and a thermally conductive inflatable means operatively coupled to the distal end of the catheter wherein the inflatable means is capable of expanding when filled with a fluid from a collapsed position into an expanded position which approximates the shape and volume of a body organ wherein the catheter is inserted a sufficient distance to place said distal end and the inflatable means which is in the collapsed position into the organ adjacent the mucosa tissue to be thermally ablated;

passing a predetermined volume of heated fluid at a selected temperature which is in a temperature range sufficient to cause thermal ablation of the mucosa layer to a predetermined thickness, from the proximal end of and through said catheter into the inflatable means to expand the same into its expanded position urging the surface of the inflatable means into intimate contact with the mucosa tissue of the organ;

controlling the period of time that the heated fluid at said selected temperature is in intimate contact with the mucosa tissue while enabling the inflatable means to thermally conduct heat from the heated fluid to the mucosa layer to ablate a predetermined thickness of tissue therefrom; and removing the heated fluid from the inflatable means after said period of time.

25. A method for performing thermal ablation of the endometrium of a uterus comprising the steps of inserting a thermal ablation apparatus, comprising a catheter having a distal end and a proximal end with an insulating means located around the catheter and a thermally conductive inflatable means operatively coupled to the distal end of the catheter wherein the inflatable means is capable of expanding when filled with a fluid from a collapsed position into an expanded position which approximates the shape and volume of a uterus into and through the vagina with the distal end thereof being positioned toward the uterus, through the cervix and into the uterus positioning the insulating means located around the catheter adjacent the walls of the vagina and with the catheter being inserted into the uterus a sufficient distance to place said distal end and inflatable means in the collapsed position in the uterus;

passing a predetermined volume of heated fluid at a selected temperature from the proximal end of and through said catheter into the inflatable means to expand the same into its expanded position urging the surface of the inflatable means into intimate contact with the endometrium of the uterus;

controlling the period of time that the heated fluid is in intimate contact with the endometrium while enabling the inflatable means to thermally conduct heat from the heated fluid to the endometrium to ablate a predetermined thickness of tissue therefrom;

controlling the depth of tissue ablation as a function of the diffusion coefficient of tissue, the temperature of the heated fluid and the time the heated fluid is held by the inflatable means in intimate contact with the endometrium; and removing the heated fluid from the inflatable means after said period of time.

26. The method of claim 25 wherein the step of controlling the time of and depth of ablation of tissue is determined in accordance with the following formulas:

$$T - Ts = -(Ts - 37) \, \text{erf} \, (x/2\sqrt{Kt}) \qquad \text{Equation No. 1}$$

wherein
T = Temperature in depth (x), function of t;
Ts = Surface temperature due to fluid
erf = error function
x = Distance into tissue from surface;
K = Diffusion coefficient of tissue; and
t = Time; and $$1 = 10^{98} \int_o^t \exp[-(75,000)/T + 273] dt. \qquad \text{Equation No. 2}$$

27. The method of claim 25 wherein the heated fluid is a saline solution and wherein the temperature of the fluid os selected to be in the range of about 122° F. (56° C.) to 211° F. (99° C.) and the predetermined period of time is selected to be in the range of about 30 seconds to about 10 minutes.

* * * * *